United States Patent [19]

Jirak et al.

[11] 4,120,307
[45] Oct. 17, 1978

[54] CARDIAC PACEMAKER

[75] Inventors: Thomas L. Jirak, Plymouth; Pieter M. J. Mulier, St. Paul, both of Minn.

[73] Assignee: Medtronic, Inc., Minneapolis, Minn.

[21] Appl. No.: 735,632

[22] Filed: Oct. 26, 1976

[51] Int. Cl.² .............................................. A61N 1/36
[52] U.S. Cl. .............................................. 128/419 PT
[58] Field of Search ....... 128/419 P, 419 PG, 419 PS, 128/419 PT, 419 R, 421, 422, 423

[56] References Cited

U.S. PATENT DOCUMENTS

| | | | |
|---|---|---|---|
| 3,557,796 | 1/1971 | Keller, Jr. et al. | 128/419 PG |
| 3,618,615 | 11/1971 | Greatbatch | 128/419 PT |
| 3,662,759 | 5/1972 | Dabolt | 128/419 PT |
| 3,738,371 | 6/1973 | Raddi et al. | 128/419 PT |
| 3,841,336 | 10/1974 | Daynard | 128/419 PT |

Primary Examiner—William E. Kamm
Attorney, Agent, or Firm—Wayne A. Sivertson

[57] ABSTRACT

Apparatus for indicating end of battery life in a cardiac pacemaker. A battery voltage monitoring circuit provides an indication of battery voltage drop below a predetermined level. A counter circuit and decode logic respond to the voltage drop indication to block a portion of a predetermined number of the generated pacing pulses from the heart to induce a benign arrhythmia in the heart thereby indicating end of battery life. In another embodiment a plurality of voltage sensors indicate progressive decreases in battery voltage and are connected with decode logic to block an increasing number of pacing pulses to indicate worsening battery condition.

57 Claims, 2 Drawing Figures

CARDIAC PACEMAKER

BACKGROUND OF THE INVENTION

Implantable electronic medical devices such as cardiac pacemakers are often powered by fully integrated power supplies which are implanted with the electronics as a single unit. When such pacemakers are implanted, there is no convenient way of testing the power supply condition to determine its present vitality or state of depletion. Because the life of the patient often depends on the proper operation of the pacemaker, which in turn is dependent on the power supply condition, it is imperative that some means of accurately determining end of power supply life be available to the patient and/or physician.

Power supply life, and the need for replacement, have been predicted on a statistically determined schedule. However, some units will fall short of the statistically determined life even with the introduction of a carefully determined safety factor. It is also considered better not to disturb or remove an implanted pacemaker which is operating properly unless absolutely necessary. Even though the surgery required for removal of an implanted pacemaker is relatively minor, the danger of complicat ons or accident is always present, and it is better avoided.

Means to indicate to a patient that the pacemaker power supply is depleted are known in the prior art, and have involved circuitry for sensing an indication of power supply depletion and linearly changing the pacemaker generator output frequency rate to a different, usually lower, frequency rate as from 70 to 65 beats per minute. This change can then be detected by a patient when taking his pulse. Many patients, however, may not be in the habit of regularly taking their pulse. Such a patient's pacemaker power supply could become dangerously depleted before he would detect that the pacemaker is operating improperly due to inadequate power. An underpowered pacer could result in serious complications, or even death.

SUMMARY OF THE INVENTION

The present invention provides apparatus for indicating to a patient that his pacemaker power supply is depleted and is nearing its end of life. The apparatus indicates power supply depletion to the patient in an inherently noticeable way that does not require constant checking by the patient such as by frequently taking his pulse. The apparatus comprises circuitry for sensing a condition of the power supply which indicates power supply depletion and for applying an arrhythmic signal to the heart to induce a benign, but noticeable arrhythmia as a warning of power supply depletion. A number of techniques of inducing a benign arrhythmia in the heart are contemplated by this invention.

One technique of inducing a benign arrhythmia in the heart is to repetitively alter the frequency of the pacemaker signal which is applied to the heart. This may be done by inducing a periodic change in the output frequency of the pacemaker signal such as by periodically blocking the pacemaker signal from the heart so that a noticeable, but benign number of pacing pulses are dropped. A benign arrhythmia may also be introduced by altering the beat rate between a plurality of different rates each operating for a short period of time, for example by changing a regular 70 b.p.m. pacing signal to alternating signals of 60 b.p.m. and 80 b.p.m., for 30 seconds each.

Where the pacing signal generated by the pacemaker constitutes a pulse train, another technique involves altering the pulse interval or interpulse period between a plurality of values. For example, a regular 830 millisecond pulse interval could be changed to alternating 600 ms. and 1000 ms. intervals. The important concept of the invention is to induce a benign, but noticeable arrhythmia in the heart.

Certain conditions, or parameters of a power supply may indicate its state of depletion on approaching end of power supply life. In a battery, for example, the output voltage will start to decrease toward the end of the battery life. The present invention particularly includes means for sensing a decrease in power supply voltage to indicate approaching end of life.

The occasion may arise in a power supply condition sensing circuit in which a spurious signal, or some other cause, may have the effect of inducing the circuit to apply an arrhythmic signal to the heart falsely indicating end cf power supply life. The present invention further includes means for disabling the arrhythmia inducing circuitry in the event that a false indication has been made. The disabling apparatus may include resetting circuitry to reset an active arrhythmia inducing circuit back to the inactive state.

Many known batteries used to power cardiac pacemakers have the characteristic of slowly reducing their voltage over a long period of time as their power is depleted. It is anticipated that a patient may ignore indications of an end of battery life for a long period of time in the belief that there is no urgency in having the depleted batteries replaced, or from a reluctance to undergo the surgery required to replace an implanted unit. Accordingly, an alternative embodiment of the invention provides progressive warnings of increasing states of battery depletion. Such warnings may be made by progressively increasing the arrhythmic aspects of the induced heart response. For example, a plurality of sensing circuits may be employed to provide indicating signals indicative of progressively decreased battery voltage which indications cause progressively operable arrhythmia inducing circuitry to alter the frequency of the generated pacemaker signal in a progressively more noticeable manner, as by increasing the length of time during which the pacemaker signal is blocked from the output to the heart. A patient may thereby receive increasingly more effective warnings as the battery becomes progressively more depleted.

BRIEF DESCRIPTION OF THE DRAWINGS

The invention may be more readily understood by reference to the following description of the preferred embodiments in which.

DESCRIPTION OF THE PREFERRED EMBODIMENTS

Figure 1:
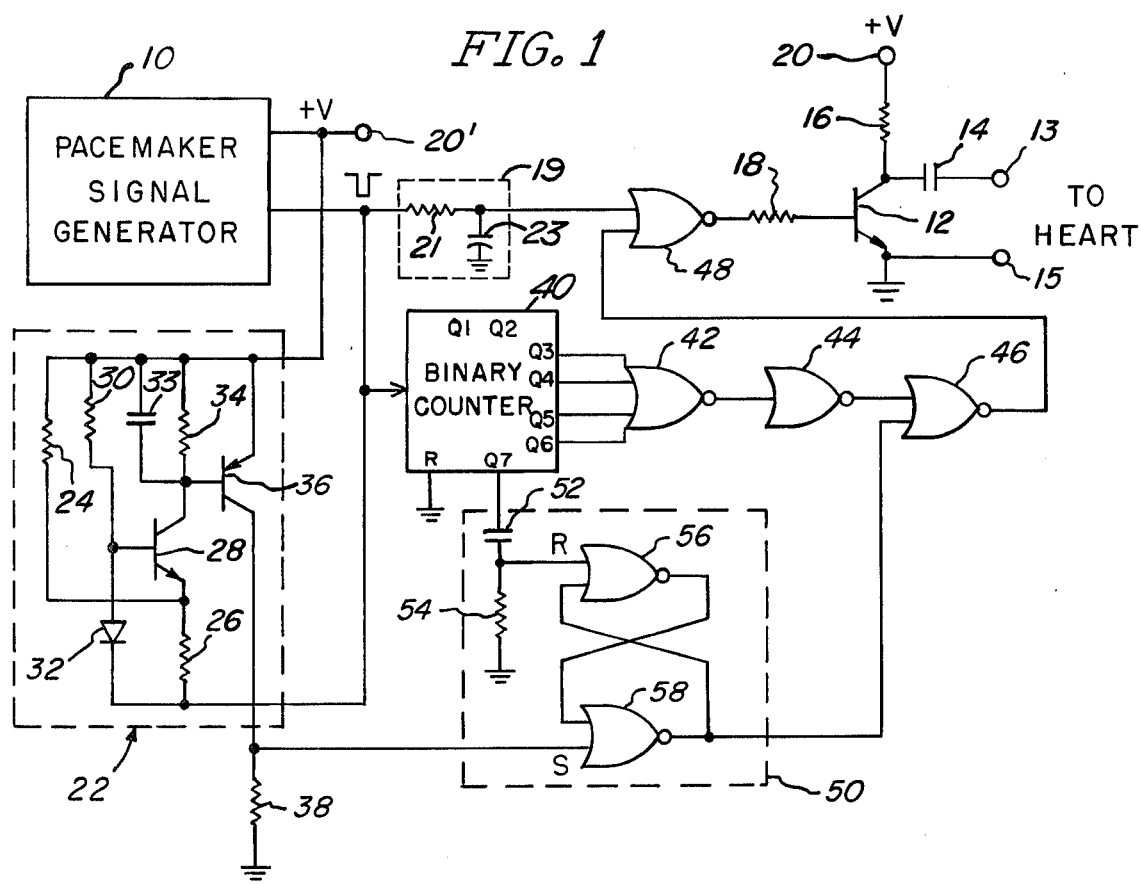
FIG. 1 shows one embodiment of the invention in combination with known pacemaker circuitry.

Referring to FIG. 1, one embodiment of the present invention is shown in combination with known pacemaker circuitry which includes a pacemaker signal generator 10 and output circuitry including a transistor 12. An output capacitor 14 is connected between the collector of transistor 12 and a terminal 13, in known manner. The emitter of transistor 12 is connected to ground and to a terminal 15, the terminals 13 and 15 being adapted for connection to a heart utilizing any type of lead suitable for carrying electrical signals to a heart. A bias resistor 16 connects the collector of the output transistor 12 to one power supply terminal 20, the terminal 20 being adapted for connection to a positive power supply (+V). An input resistor 18 is connected to the base of transistor 12. The power supply may comprise batteries or other known sources of power suitable for use with heart pacemakers and the output circuitry described to this point is known to those familiar with the art.

The present invention senses a change in power supply condition to determine depletion of the power supply and give an indication of the end of power supply life utilizing novel circuitry to provide an inherent indication to a patient that the power supply is becoming depleted. A voltage sensing trip circuit 22 is connected to a power supply terminal 20'. One parameter of a battery supply which may be monitored to determine the state of depletion is battery output voltage. As the battery becomes depleted, the output voltage decreases. By monitoring the output voltage, circuit 22 provides an indicating signal when the battery voltage drops to a predetermined level.

Sensing circuit 22 includes resistors 24, 30 and 34 and capacitor 33 connected to a power supply terminal 20'. The emitter of a transistor 36 is also connected to the same terminal 20' and capacitor 33 and resistor 34 are connected to the base of transistor 36, which is also connected to the collector of a transistor 28. The base of transistor 28 is connected to resistor 30 and the emitter of transistor 28 is connected to resistor 24. Resistor 26 is also connected to the emitter of transistor 28. A diode 32 is connected to the base of transistor 28 and also to resistor 26 to form a common terminal with resistor 26 which is connected to the output of pacemaker signal generator 10. The collector of transistor 36 is connected to a resistor 38 which is connected to ground. The collector of transistor 36 comprises the output of circuit 22. Resistors 24 and 26 form a voltage divider for biasing the emitter of transistor 28. Diode 32, in parallel with the base-emitter junction of transistor 28 and resistor 26, has essentially the same temperature coefficient as the base-emitter junction of transistor 28 to reduce temperature sensitivity of circuit 22 to a minimum.

The pacemaker signal generator 10 produces a train of negative-going pulses, in known manner, one of which is shown at the output terminal of generator 10. The common terminal connection of diode 32 and resistor 26 is connected back to the output terminal of the pacemaker signal generator 10 so that, when the negative-going output pulses of pacemaker signal generator 10 are produced, circuit 22 will be enabled by being effectively grounded through the output stage (not shown) of generator 10. Thus, a significant reduction in power consumption by circuit 22 is produced since it is drawing power only when a pacing pulse is generated. Further reduction in power consumption by circuit 22 may be had by building the circuity using CMOS logic devices as will be understood by those skilled in the art.

The output of pacemaker signal generator 10 is also connected to the trigger input of binary counter 40. The output signal pulses are counted by binary counter 40 which in this preferred embodiment, has seven stages to count up to 128 pulses, and then return to Zero for recount. A portion of the plurality of stages of counter 40 are connected to the inputs of a NOR gate 42. In this embodiment the third through the sixth stages ($Q_3$ to $Q_6$) are connected to the four inputs of NOR gate 42, which provides a high output signal when all of the inputs, i.e., the stages of counter 42 which are connected to it, are low. The output of NOR gate 42 is connected to NOR gate 44 for inverting the output signal of NOR gate 42, the output of NOR gate 44 being connected to one input of NOR gate 46. The other input of NOR gate 46 is connected to receive an indicating signal from voltage sensor trip circuit 22 in a manner to be described below. The output of NOR gate 46 is connected to one input of NOR gate 48. The other input of NOR gate 48 is connected to the output of pacemaker signal generator 10 via an RC delay 19 formed of resistor 21 and capacitor 23. The output of NOR gate 48 is connected to resistor 18 to be received by output transistor 12 to be applied for pacing the heart.

The highest stage of binary counter 40, in this embodiment the seventh stage ($Q_7$), is connected to a reset circuit 50 which is also connected between the collector of transistor 36 and the other input of gate 46. Reset circuit 50 comprises an RS flip-flop composed of NOR gates 56, 58. One input of NOR gate 56 comprises the R input of the flip-flop. The other input of NOR gate 56 is connected to the output of NOR gate 58. The output of NOR gate 56 is connected to one input of NOR gate 58. The other input of NOR gate 58 comprises the S input of the flip-flop. A capacitor 52 is connected in series with a resistor 54 between stage $Q_7$ of counter 40 and ground. The R input of the flip-flop is connected between capacitor 52 and resistor 54. Capacitor 52 is connected to stage $Q_7$ of binary counter 40 for triggering the R input of the flip-flop. The S input is connected to the collector of transistor 36 to be triggered by the presence of a signal produced by sensor circuit 22 indicating a drop in power supply voltage to a predetermined level. While it has been found convenient to construct the flip-flop of a pair of NOR gates, any other form of RS flip-flop may be used.

The operation of the circuit of FIG. 1 is as follows: pacemaker signal generator 10 generates a train of negative-going pulses to be applied to a heart by output transistor 12 through terminals 13, 15. Each time a pulse is produced by signal generator 10, voltage sensor trip circuit 22 is activated by being effectively grounded through the output stage (not shown) of signal generator 10. The generated pulse train is simultaneously counted by binary counter 40. When the voltage at battery terminal 20' has dropped below a predetermined level, as determined by voltage divider 24, 26, transistor 28, normally off, is turned on, thereby turning on transistor 36 to produce an indicating signal across resistor 38. Capacitor 33 supresses transient signals that would otherwise occur at the edges of each output pulse of signal generator 10 and which would turn on transistor 36 without regard to battery voltage. When there is a voltage across resistor 38, the output of NOR gate 58 is low.

As will be understood by those skilled in the art, during the first four counts made by counter 40, the outputs of stages $Q_3$, $Q_4$, $Q_5$, and $Q_6$, are low, thereby producing a high at the output of NOR gate 42, which is inverted by NOR gate 44 to a low, and applied to NOR gate 46. When lows are present on both inputs of NOR gate 46, one from NOR gate 44 and one from the output of NOR gate 58 in flip-flop 50, the output of gate 46 is high thereby causing gate 48 to block the signals produced by signal generator 10 from reaching output transistor 12. This occurs during the first four counts made by counter 40 if an indicating signal of battery depletion is applied to flip-flop 50 by sensor circuit 22. In this manner, a benign arrhythmia is induced in the heart to warn the patient that the pacemaker power supply (a battery in this embodiment) is becoming depleted. The RC delay 19 compensates for delay inherent in sensing circuit 22 so that the pulse from signal generator 10 does not arrive at gate 48 until gate 48 is in the correct blocking or not blocking state.

It is considered possible that voltage sensor trip circuit 22 could become accidentally tripped by a spurious signal or some other cause to produce a signal falsely indicating a depleted battery. In order to reset gate 48 to the non-blocking condition under the circumstances where a false indication has been introduced momentarily into the circuit, reset circuit 50 is connected to the stage $Q_7$ of binary counter 40. Normally, when an indicating signal is present at the S input of NOR gate 58, the output of gate 58 is low. The state of the output of gate 56 cannot affect this since a high output on a NOR gate such as gate 58 can only be obtained when both inputs are low. Therefore, when the count reaches 64 and a high input pulse is applied to the R input of gate 56, the output of gate 58 remains unchanged. When no input high is present at the R input of gate 56 and the output of gate 58 is low, the output of gate 56 is high. However, if no high voltage indicating signal is present across resistor 38, one input of gate 58 will be low. When a pulse is applied to the R input of gate 56, the output goes low because its other input is low, the output of gate 58 being low. This causes gate 58 to go high because no high indicating signal is present at the S input. A high at the output of gate 58 applied to gate 46 causes the output of gate 46 to go low, thereby unblocking gate 48 even during the first four counts made by the counter. Reset circuit 50 thus disables the blocking effect of the invention by resetting gate 48 to an inactive or unblocking state.

Figure 2:
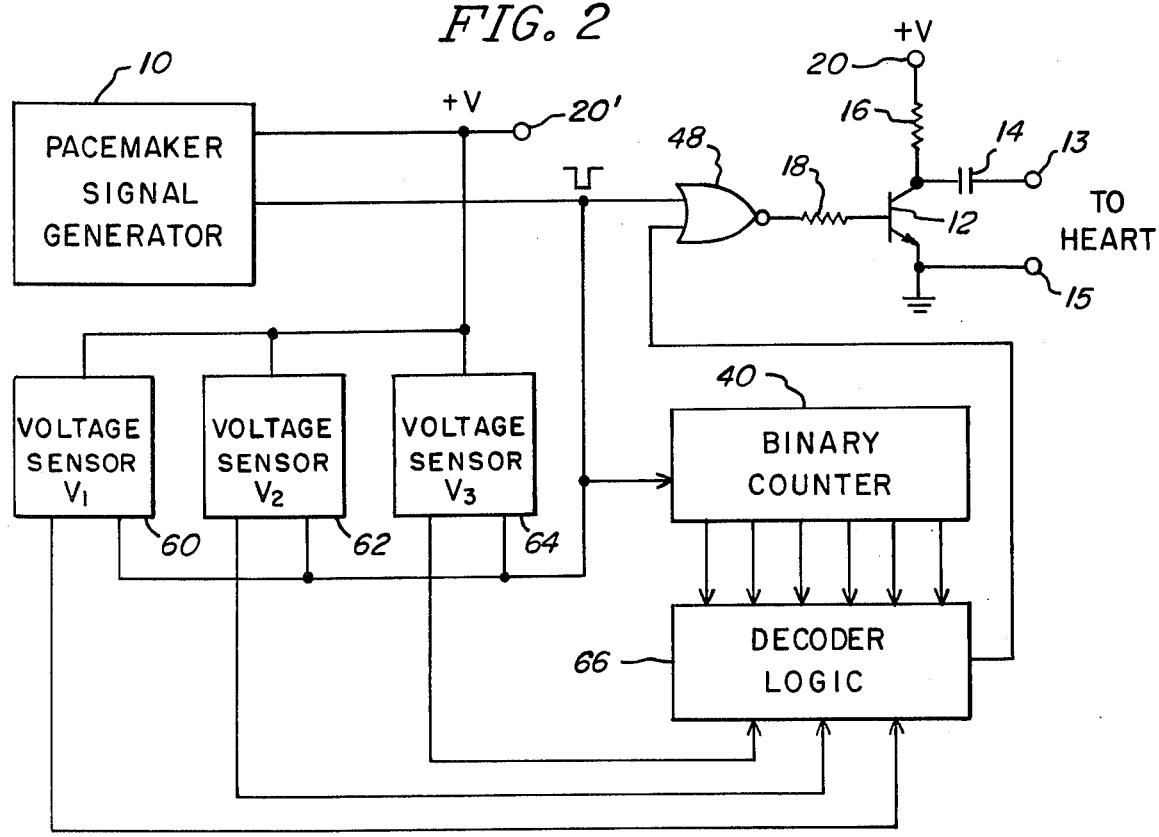
FIG. 2 shows another embodiment of the invention for sensing of progressive changes in power supply condition.

Referring to FIG. 2, an alternative embodiment is shown in which like numbered elements are common to the embodiment of FIG. 1. FIG. 2 includes a pacemaker signal generator 10 connected to one input of a NOR gate 48 having an output connected to a transistor 12 biased by resistors 16 and 18 with output capacitor 14 connected to the collector for applying a pacing signal to a heart at terminals 13 and 15 as previously described.

Since many known power supplies, such as certain types of batteries commonly used to power pacemakers, degenerate slowly, it is possible for a patient to assume that the benign arrhythmia induced by the circuit of FIG. 1 does not indicate the necessity for prompt battery replacement. The embodiment of FIG. 2 gives a progressively more noticeable warning in response to progressive power supply depletion. Three voltage sensor trip circuits 60, 62, 64 are connected to power supply terminal 20' and to the output of pacemaker signal generator 10. Each voltage sensor circuit 60, 62, 64 is similar to circuit 22 of FIG. 1, except that each sensor circuit is designed to produce an indicating signal at a different voltage level so that, for example, voltage sensor circuit 60 would give an indication at one voltage level, voltage sensor circuit 62 would give an indication at a lower voltage level, and voltage sensor circuit 63 would give an indication at an even lower voltage level. Each sensor circuit may be designed to give an indication of battery depletion at a desired voltage level by adjusting the ratios of resistance values between the resistors corresponding to resistors 24, 26 in circuit 22.

A binary counter 40 is also connected to the output of generator 10. Binary counter 40 counts pacemaker signal generator output pulses as previously described with respect to FIG. 1. It may have the same number of stages as the counter in FIG. 1 or a different number of stages as desired for the particular application. The number of stages is determined by what portion of a count of a predetermined plurality of pulses generated by pulse generator 10 is to be blocked to give suitable notice to a patient of end of battery life.

The outputs of voltage sensor circuits 60, 62, 64 corresponding to the collector of transistor 36 in FIG. 1 and the output of each stage of binary counter 40 are connected to decode logic 66 which may be comprised of a group of gates in combination with a group of reset circuit 50, as illustrated in FIG. 1, one switch for each voltage sensor used. The output of decode logic 66 is connected to the other input of NOR gate 48. The gates of decode logic 66 are connected to the counter in such a way that, as each group of gates is triggered by an indicating signal from its respective voltage sensor circuit, a predetermined count of pulses is blocked from the output by gate 48. Given the teachings of FIG. 1, a person of ordinary skill in the art may construct a specific embodiment in accordance with FIG. 2 and the operational characteristics described below.

In the embodiment of FIG. 2, as the output voltage of the power supply diminishes to each level progressively sensed by the respective voltage sensor trip circuit 60, 62, 64, an increasing number of pulses as determined by decode logic 66 are blocked from the output to the heart to create a more effective warning of power supply depletion. So, for example, when the voltage of sensor circuit 60 is reached, two pulses in every 64 may be blocked. As the power supply diminishes further to the voltage level of voltage sensor 62, an additional two pulses may be blocked, and as the power supply progressively diminishes to the level of voltage sensor 64, a total of six or eight pulses may be blocked from the output thereby creating a progressively more noticeable benign arrhythmia to warn the patient that the power supply is becoming progressively more depleted.

Certain specific embodiments of this invention have been constructed and have been found to operate satisfactorily. By way of example, the following values and component designations have been used to construct one working example of the embodiment of FIG. 1 with a power supply of 5.4 volts:

| Circuit Elements | | Component Designations | Circuit Elements | Component Designations |
|---|---|---|---|---|
| Resistors: | 16 | 10 K ohms | Diode: | 32 MLED 600*** |
| | 18 | 12 K ohms | | |
| | 21 | 100 K ohms | | |
| | 24 | 300 K ohms | Gates: | 42, 44 SSS 4204** |
| | 26 | 100 K ohms | | CMOS dual NOR |
| | 30 | 220 K ohms | 46, 48, 56, 58 | CD 4001A* |
| | 34 | 1 M ohm | | CMOS quad NOR |
| | 38 | 1 M ohm | | |
| | 54 | 1 M ohm | | |
| Capacitors: | 14 | 10 pf | Binary Counter 40 | CD 4024A* CMOS ripple counter |
| | 23 | 0.01 | | |
| | 33 | 1000 pf | | |
| | 52 | 510 pf | | |

-continued

| Circuit Elements | Component Designations | Circuit Elements | Component Designations |
| --- | --- | --- | --- |
| Transistors: 12 | ZN 3700 | | |
| 28 | ZN 2484 | | |
| 36 | ZN 2907 | | |

*RCA products
**Solid State Scientific Product
***Motorola Product

It is to be understood that, within the scope of the appended claims, modifications and variations of the illustrated embodiments are contemplated by the present invention. For example, the voltage sensor trip circuits may be replaced by any circuit capable of detecting a power supply condition indicative of power supply deterioration to produce an indicating signal when that condition reaches a certain level. Also, the concept of the present invention includes applying any form of benign arrhythmia inducing signal to the heart in response to a sensed power supply deterioration. For example, instead of periodically blocking pacing pulses, circuitry responsive to the condition indicating signal may be employed to alter the output frequency between different frequency rates as by connecting switching circuitry to the timing circuitry of the signal generator, the switching circuitry being responsive to the condition indicating signal to alter the signal generator timing characteristics. Other variations may include the changing of the timing of both stages of an astable multivibrator employed as the signal generator to produce alternating pulses of different pulse intervals with one or more pulses of each interval being applied as an output pulse before switching to the alternate interval. Any suitable circuit elements and systems which perform the functions described herein may be used within the scope of the present invention.

As will be understood, this invention is suitable for use with any known pacemaker, such as asynchronous, demand or synchronous. For a more particular understanding of what is considered to be the scope of this invention, reference is made to the appended claims.

What is claimed is:

1. Apparatus for use with a signal generating pacemaker having a power supply and output means adapted for connection to a heart, comprising: first means for sensing a change in power supply condition; and second means connected and responsive to the first means for repetitively applying a benign arrhythmia inducing arrhythmic signal to the output means in response to a change in power supply condition.

2. Apparatus according to claim 1 wherein the second means comprises means for altering the frequency of the pacemaker output signal.

3. Apparatus according to claim 1 wherein the second means comprises means for periodically altering the frequency of the pacemaker output signal between at least first and second frequencies.

4. Apparatus according to claim 3 wherein the frequency altering means comprises means for periodically blocking the generated pacemaker signal from the output means.

5. Apparatus according to claim 1 wherein the first means comprises means for sensing a decrease in power supply voltage.

6. Apparatus according to claim 5 wherein the means for sensing a decrease in power supply voltage comprises: voltage divider means adapted for connection to the power supply; and switching means connected between the voltage divider means and the second means for providing a signal to the second means to indicate a drop in power supply voltage.

7. Apparatus according to claim 1 wherein the first means comprises means for sensing progressive changes in power supply condition.

8. Apparatus according to claim 7 wherein the means for sensing progressive changes in power supply condition comprises means for sensing progressive decreases in power supply voltage.

9. Apparatus according to claim 7 wherein the second means comprises means responsive to the means for sensing progressive changes in power supply condition for periodically altering the frequency of the pacemaker output signal in a progressive manner.

10. Apparatus according to claim 9 wherein the means for periodically altering the frequency of the pacemaker output signal in a progressive manner comprises means for periodically blocking the generated pacemaker signal from the output means for time periods of progressively changing length.

11. Apparatus according to claim 10 wherein: the means for sensing progressive changes in power supply condition comprises a plurality of means for sensing progressive decreases in power supply voltage; and the means for periodically blocking the generated pacemaker signal comprises means responsive to the plurality of sensing means for blocking the generated pacemaker signal from the output means for time periods of respectively increasing length.

12. Apparatus according to claim 11 wherein each of the plurality of sensing means comprises: voltage divider means adapted for connection to the power supply; and switching means connected between the voltage divider means and the means for periodically blocking the pacemaker signal for providing a signal to the means for periodically blocking the generated pacemaker signal to indicate a drop in power supply voltage to a predetermined level.

13. Apparatus for use with a stimulating pulse train generating pacemaker having a power supply and output means adapted for connection to a heart, comprising: first means for sensing a change in power supply condition; and second means connected and responsive to the first means for repetitively altering the period between stimulating pulses of the generated pulse train applied to the output means between at least first and second periods.

14. Apparatus according to claim 13 wherein the first means comprises means for sensing a decrease in power supply voltage.

15. Apparatus according to claim 14 wherein the means for sensing a decrease in power supply voltage comprises: voltage divider means adapted for connection to the power supply; and switching means connected between the voltage divider means and the second means for providing a signal to the second means to indicate a drop in power supply voltage.

16. Apparatus according to claim 13 wherein the second means comprises: counter means for counting a plurality of pulses generated by the pacemaker; and gate means connected for responding to the first means to block a portion of the plurality of counted pulses.

17. Apparatus according to claim 16 wherein the counter means comprises binary counter means having a plurality of stages.

18. Apparatus according to claim 17 wherein the gate means comprises: a first gate having an output terminal and a plurality of input terminals connected to at least some of the plurality of stages of the binary counter means; and a second gate having an output and having two inputs connected to the output terminal of the first gate and to the first means.

19. Apparatus according to claim 18 wherein the gate means further comprises a third gate connected to the output of the second gate for blocking the generated pacemaker pulse train from the output means.

20. Apparatus according to claim 13 wherein the first means comprises means for sensing progressive changes in power supply condition.

21. Apparatus according to claim 20 wherein the means for sensing progressive changes in power supply condition comprises means for sensing progressive decreases in power supply voltage.

22. Apparatus according to claim 13 wherein the means for periodically altering the period between pulses of the generated pulse train applied to the output means comprises means for periodically blocking the generated pacemaker pulse train from the output means.

23. Apparatus according to claim 22 wherein the sensing means comprises: voltage divider means adapted for connection to the power supply; and switching means connected between the voltage divider means and the blocking means for providing a signal to the blocking means to indicate a drop in power supply voltage to a predetermined level.

24. Apparatus according to claim 22 wherein the first means comprises means for sensing progressive changes in power supply condition.

25. Apparatus according to claim 24 wherein the blocking means comprises: counter means for counting a plurality of pulses generated by the pacemaker; and decode means connected for responding to the sensing means for blocking a portion of the plurality of counted pulses for progressively increasing length of time in response to the sensing of progressive decreases in power supply voltage.

26. In signal generator means of the type having output means, a power supply, and means responsive to a condition of the power supply to alter the generator means output signal, the improvement wherein the responsive means comprises means for repetitively applying a benign arrhythmia inducing arrhythmic signal to the output means in response to a change in a power supply condition.

27. Generator means according to claim 26 wherein the applying means comprises means for periodically blocking the generator means output signal from the output means.

28. Generator means according to claim 27 wherein the responsive means further comprises: voltage divider means adapted for connection to the power supply; and switching means connected between the voltage divider means and the blocking means for providing a signal to the blocking means to indicate a drop in power supply voltage.

29. Generator means according to claim 28 wherein the blocking means comprises: counter means for counting a plurality of pulses generated by the generator means; and gate means connected to the switching means for blocking a portion of the plurality of counter pulses in response to the indicating signal.

30. Generator means according to claim 29 wherein the counting means comprises binary counter means having a plurality of stages.

31. Generator means according to claim 30 wherein the gate means comprises: first gating means having an output terminal and a plurality of input terminals connected to at least some of the plurality of stages of the binary counter means; and second gating means connected to the output terminal of the first gating means and to the switching means.

32. Generator means according to claim 31 wherein the gate means further comprise third gating means connected to the output of the second gating means and between the signal generator means output and the output means for blocking the signal generator means output signal from the output means.

33. Generator means according to claim 26 wherein the responsive means further comprises voltage divider means adapted for connection to the power supply and switching means connected between the voltage divider means and the applying means for providing a signal to the applying means to indicate a drop in power supply voltage.

34. Generator means according to claim 26 wherein the responsive means comprises means for sensing progressive changes in power supply condition.

35. Generator means according to claim 34 wherein the responsive means further comprises means connected to the means for sensing progressive changes in power supply condition for progressively altering the frequency of the generator means output signal applied to the output means.

36. Generator means according to claim 35 wherein the means for progressively altering the frequency of the generator means output signal applied to the output means comprises means for periodically blocking the generator means output signal from the output means for time periods of progressively changing length.

37. Generator means according to claim 36 wherein the means for sensing progressive changes in power supply condition comprises a plurality of means for sensing progressive decreases in power supply voltage; and the blocking means comprises means responsive to the plurality of sensing means for blocking the generator means output signal from the output means for time periods of progressively increasing length.

38. Generator means according to claim 37 wherein each of the plurality of sensing means comprises: voltage divider means connected to the power supply; and switching means connected between the voltage divider means and the blocking means for providing a signal to the blocking means to indicate a drop in power supply voltage to a predetermined level.

39. Generator means according to claim 26 wherein the signal generator means includes means for generating a train of pulses.

40. Generator means according to claim 39 wherein the responsive means further comprises: a plurality of means for sensing progressive decreases in power supply voltage; and means responsive to the plurality of sensing means for blocking the generated pulse train from the output means for time periods of progressively increasing length.

41. Generator means according to claim 40 wherein each of the plurality of sensing means comprises: voltage divider means connected to the power supply; and switching means connected between the voltage divider means and the blocking means for providing a signal to the blocking means to indicate a drop in power supply voltage to a predetermined level.

42. Generator means according to claim 40 wherein the blocking means comprises: counter means for mounting a the number of pulses in said pulse train and decode means connected and responsive to the plurality of sensing means for blocking a portion of the counted pulses for progressively increasing lengths of time in response to the respective means for sensing progressive decreases in power supply voltage.

43. Apparatus for use with a signal generating pacemaker having a power supply and output means adapted for applying a signal to a heart comprising: first means for producing an indicating signal in response to a change in power supply condition; second means responsive to the first means for applying an arrhythmia inducing arrhythmic signal to the output means; said third means connected between the first means and the second means for disabling the second means in the absence of an indicating signal from the first means.

44. Apparatus according to claim 43 wherein: the second means comprises means having an active and an inactive state, the second means being responsive to the first means indicating signal for applying the arrhythmic signal to the output means in the active state; and the third means comprises means for resetting the second means to the inactive state in the absence of said indicating signal.

45. Apparatus according to claim 44 wherein the second means comprises means for altering the frequency of the signal applied to the output means.

46. Apparatus according to claim 44 wherein the second means comprises means for periodically altering the frequency of the signal applied to the output means.

47. Apparatus according to claim 46 wherein the altering means comprises means for periodically blocking the generated pacemaker signal from the output means.

48. Apparatus according to claim 43 wherein the first means comprises means for sensing a decrease in power supply voltage.

49. Apparatus according to claim 48 wherein the means for sensing a decrease in power supply voltage comprises: voltage divider means adapted for connection to the power supply; and switching means connected to the voltage divider means for providing a signal to the second means to indicate a drop in power supply voltage.

50. Apparatus for use with a stimulating pulse train generating pacemaker having a power supply and output means adapted for applying a signal to a heart comprising: first means for producing an indicating signal in response to a change in power supply condition; second means responsive to the first means comprising means for repetitively altering the frequency of the stimulating pulse train applied to the output means between at least first and second frequencies; and third means connected between the first means and the second means for disabling the second means in the absence of an indicating signal from the first means.

51. Apparatus according to claim 50 wherein: the second means comprises means having an active and an inactive state and responsive to the first means indicating signal for blocking the generated pulse train from the output means in the active state; and the third means comprises means for resetting the second means to the inactive state in the absence of said indicating signal.

52. Apparatus accdicording to claim 50 wherein the first means comprises means for sensing a decrease in power supply voltage.

53. Apparatus according to claim 52 wherein the means for sensing a decrease in power supply voltage comprises: voltage divider means adapted for connection to the power supply; and switching means connected to the voltage divider means for providing a signal to the second means to indicate a drop in power supply voltage.

54. Apparatus according to claim 50 wherein: the second means comprises counter means for counting a plurality of pulses generated by the pacemaker and gate means connected for responding to the first means to block a portion of the plurality of counted pulses; and the third means comprises reset means connected to the counter means, the gate means and the first means for unblocking the gate means after a predetermined pulse count in the absence of the indicating signal.

55. Apparatus according to claim 54 wherein the counter means comprises binary counter means having a plurality of stages, the reset means being connected to at least one stage thereof corresponding to the predetermined pulse count.

56. Apparatus according to claim 55 wherein the gate means comprises: first gating means having an output terminal and a plurality of input terminals connected to those stages of the binary counter means corresponding to said portion of the plurality of counted pulses; and second gating means connected to the output terminal of the first gating means and to the reset means, the reset means being connected to the first means.

57. Apparatus according to claim 56 wherein the reset means comprises: bistable switching means with set and reset inputs and an output; the set input being connected to the first means, the reset input being connected to one stage of the counter means and the output being connected to the second gating means, the second gating means being reset to the inactive state by the reset means when the binary counter means reaches said predetermined count of pulses in the absence of the indicating signal.

* * * * *